United States Patent
Poulaki et al.

(10) Patent No.: US 8,658,633 B2
(45) Date of Patent: Feb. 25, 2014

(54) METHODS AND COMPOSITIONS FOR TREATING CONDITIONS OF THE EYE

(75) Inventors: Vasiliki Poulaki, Roslindale, MA (US); Joan W. Miller, Winchester, MA (US); Evangelos S. Gragoudas, Lexington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 1049 days.

(21) Appl. No.: 11/654,892

(22) Filed: Jan. 18, 2007

(65) Prior Publication Data

US 2007/0191917 A1     Aug. 16, 2007

Related U.S. Application Data

(60) Provisional application No. 60/773,890, filed on Feb. 16, 2006.

(51) Int. Cl.
*A61K 31/555*     (2006.01)

(52) U.S. Cl.
USPC .......................................... 514/187; 514/912

(58) Field of Classification Search
USPC .................................................. 514/187, 912
See application file for complete search history.

(56) References Cited

U.S. PATENT DOCUMENTS

| | | | |
|---|---|---|---|
| 4,261,989 A | 4/1981 | Sasaki et al. |
| 4,738,958 A | 4/1988 | Franco et al. |
| 5,756,541 A | 5/1998 | Strong et al. |
| 5,798,349 A | 8/1998 | Levy et al. |
| 5,910,510 A | 6/1999 | Strong et al. |
| 5,958,892 A | 9/1999 | Mukhopadhyay et al. |
| 5,968,921 A | 10/1999 | Gold |
| 6,015,803 A | 1/2000 | Wirostko |
| 6,210,974 B1 | 4/2001 | Gold |
| 6,225,303 B1 | 5/2001 | Miller et al. |
| 6,245,759 B1 | 6/2001 | Bilodeau et al. |
| 6,306,874 B1 | 10/2001 | Fraley et al. |
| 6,313,138 B1 | 11/2001 | Fraley et al. |
| 6,410,029 B1 | 6/2002 | Mukhopadhyay et al. |
| 6,420,382 B2 | 7/2002 | Fraley et al. |
| 6,479,512 B1 | 11/2002 | Fraley et al. |
| 6,544,988 B1 | 4/2003 | Bilodeau et al. |
| 6,586,423 B2 | 7/2003 | Bilodeau et al. |
| 6,586,424 B2 | 7/2003 | Bilodeau et al. |
| 6,613,506 B1 | 9/2003 | Holzmayer et al. |
| 6,641,810 B2 | 11/2003 | Gold |
| 6,656,942 B2 | 12/2003 | Kim et al. |
| 6,696,483 B2 | 2/2004 | Singh |
| 6,734,211 B1 | 5/2004 | Gold |
| 6,794,393 B1 | 9/2004 | Fraley et al. |
| 6,872,724 B2 | 3/2005 | Zhao et al. |
| 6,875,767 B2 | 4/2005 | Bilodeau et al. |
| 6,927,293 B2 | 8/2005 | Kim et al. |
| 7,138,402 B2 | 11/2006 | Kasibhatla et al. |
| 2005/0267087 A1 | 12/2005 | Poulaki et al. |

FOREIGN PATENT DOCUMENTS

WO    WO-2007/097839     8/2007

OTHER PUBLICATIONS

Seo et al., American Journal of Pathalogy 1999; 154: 1743-1753.*
Stewart et al. (2011) "Comparison of choroidal and retinal endothelial cells: Characteristics and response to VEGF isoforms and anti-VEGF treatments," Experimental Eye Research 93:761-766.
Bressler et al. (1988) "Age-related macular degeneration," Surv. Ophthalmol. 32: 375-412.
Eyetech Study Group (2003) "Anti-vascular Endothelial Growth Factor Therapy for Subfoveal Choroidal Neovascularization Secondary to Age-related Macular Degeneration: Phase II Study Results," Ophthalmology 110(5): 979-86.
Ferrario et al. (2000) "Antiangiogenic treatment enhances photodynamic therapy responsiveness in a mouse mammary carcinoma," Cancer Res. 60: 4066-69.
Freund et al. (1993) "Age-related macular degeneration and choroidal neovascularization," Amer. J. Ophthalmol. 115(6): 786-91.
Goetz et al. (2003) "The Hsp90 chaperone complex as a novel target for cancer therapy," Ann. Oncol. 14(8): 1169-76.
Guyer et al. (1986) "Subfoveal choroidal neovascular membranes in age-related macular degeneration. Visual prognosis in eyes with relatively good initial visual acuity," Arch. Ophthalmol. 104: 702-05.
Hyman et al. (1983) "Senile macular degeneration: a case-control study," Am. J. Epidemiol. 118: 213-27.
International Search Report for PCT/US2007/001264, published Oct. 25, 2007 (5 pages).
Isaacs et al. (2003) "Heat shock protein 90 as a molecular target for cancer therapeutics," Cancer Cell 3: 213-17.
Klein & Klein (1982) "Therapy of basal cell carcinoma in the anorectal region," Arch. Ophthalmol. 100: 571-573.
Kociok et al. (2005) "Geldanamycin Treatment Reduces Neovascularization in a Mouse Model of Retinopathy of Prematurity," Invest. Ophthalmol. Vis. Sci. 46: 4105, E-Abstract B463 (corresponding abstract first available Feb. 22, 2005, at ARVO website, www.arvo.org) (1 page).
Leibowitz et al. (1980) "The Framingham Eye Study monograph: An ophthalmological and epidemiological study of cataract, glaucoma, diabetic retinopathy, macular degeneration, and visual acuity in a general population of 2631 adults, 1973-1975," Surv. Ophthalmol. 24: 335-610 (5 pages enclosed, including Table of Contents and preface).
Macular Photocoagulation Study Group (1991) "Laser photocoagulation of subfoveal neovascular lesions in age-related macular degeneration: Results of a randomized clinical trial," Arch. Ophthalmol. 1991, 109:1220-31.
Maloney et al. (2002) "HSP90 as a new therapeutic target for cancer therapy: the story unfolds," Expert Opin. Biol. Ther. 2(1):3-24.

(Continued)

Primary Examiner — Zohreh Fay
(74) Attorney, Agent, or Firm — Goodwin Procter LLP

(57) ABSTRACT

Provided are methods and compositions for treating ocular conditions characterized by the presence of unwanted choroidal neovasculature, for example, neovascular age-related macular degeneration. The selectivity and sensitivity of, for example, a photodynamic therapy (PDT)-based approach can be enhanced by combining the PDT with an ansamycin analog or heat shock protein 90 inhibitor, for example, 17-allylamino-17-demethoxygeldanamycin.

16 Claims, No Drawings

(56) References Cited

OTHER PUBLICATIONS

Miller et al. (1999) "Photodynamic therapy with verteporfin for choroidal neovascularization caused by age-related macular degeneration: Results of a single treatment in a phase 1 and 2 study," Arch. Ophthalmol. 117: 1161-73.

Munster et al. (2001) "Inhibition of heat shock protein 90 function by ansamycins causes the morphological and functional differentiation of breast cancer cells," Cancer Res. 61(7): 2945-52.

Poulaki et al. (2003) "Regulation of vascular endothelial growth factor expression by insulin-like growth factor I in thyroid carcinomas," J. Clin. Endocrinol. Metab. 88(11): 5392-98.

Poulaki et al. (2004) "Insulin-like growth factor-I plays a pathogenetic role in diabetic retinopathy," Amer. J. of Pathol. 165(2): 457-468.

TAP Report 2 (2001) "Treatment of Age-related macular Degeneration with Photodynamic Therapy (TAP) Study Group. Photodynamic therapy of subfoveal choroidal neovascularisation in age-related macular degeneration with verteporfin. Two year results of two randomized clinical trails—TAP report 2," Arch Ophthalmol 119: 198-207.

Volanti et al. (2002) "Involvement of Oxidative Stress in NF-kappaB activation in endothelial cells treated by photodynamic therapy," Photochemistry and Photobiology 75(1): 36-45.

Zacks et al. (2002) "Verteporfin photodynamic therapy in the rat model of choroidal neovascularization: angiographic and histologic characterization," Invest. Ophthalmol. Vis. Sci. 43(7): 2384-91.

Adamis et al. (1996) "Inhibition of vascular endothelial growth factor prevents retinal ischemia-associated iris neovascularization in a non-human primate," Arch. Ophthalmol. 114(1): 66-71.

Aiello et al. (1994) "Vascular endothelial growth factor in ocular fluid of patients with diabetic retinopathy and other retinal disorders," M. Engl. J. Med. 331(22): 1480-87.

Brooks et al. (1994) "Requirement of vascular integrin alpha v beta 3 for angiogenesis," Science 264(5158): 569-71.

Conde et al. (1997) "Induction of heat shock proteins by tyrosine kinase inhibitors in rat cardiomyocytes and myogenic cells confers protection against simulated ischemia," J. Mol. Cell. Cardiol. 29(7): 1927-38.

Folkman (1995) "Angiogenesis in cancer, vascular, rheumatoid, and other disease," Nat. Med. 1(1): 27-31.

Friedlander et al. (1995) "Definition of two angiogenic pathways by distinct alpha v integrins," Science 270(5421): 1500-02.

Garcia-Garcia et al. (2001) "Phosphatidylinositol 3-kinase and ERK are required for NF-kappaB activation byt not for phagocytosis," J. Leukoc. Biol. 70(4): 649-58.

Poulaki et al. (2006) "Geldanamycin Treatment Reduces Choroidal Neovascularization in a Murine Model," Invest. Ophthalmol. Vis. Sci. 47: E-Abstract B1038 (corresponding abstract first available Feb. 17, 2006, at ARVO website, www.arvo.org) (1 page).

Hostein et al. (2001) "Inhibition of signal transduction by the HSP90 inhibitor 17-allylamino-17-demethoxygeldanamycin results in cytostatis and apoptosis," Canc. Res. 61: 4003-06.

Levy et al. (1995) "Transcriptional regulation of the rat vascular endothelial growth factor gene by hypoxia," J. Biol. Chem. 270: 13333-40.

Malhotra et al. (2001) "Geldanamycin inhibits NF-kappaB activation and interleukin-8 gene expression in cultured human respiratory epithelium," Am. J. Respir. Cell Mol. Biol. 25(1): 92-97.

Munster et al. (2001) "Modulation of Hsp90 Function by ansamycins sensitizes breast cancer cells to chemotherapy-induced apoptosis in an RB and schedule-dependent manner," Clin. Canc. Res. 7: 2228-36.

Munster et al. (2002) "Degradation of HER2 by ansamycins induces growth arrest and apoptosis in cells with HER2 overexpression via HER3, phosphatidylinositol 3'-kinase-AKT-dependent pathway," Canc. Res. 62: 3132-37.

Poulaki et al. (2002) "Acute intensive insulin therapy exacerbates diabetic blood-retinal barrier breakdown via hypoxia-inducible factor-1-alpha and VEGF," J. Clin. Invest. 109(6): 805-15.

Stebbins et al. (1997) "Crystal structure of an Hsp90-geldanamycin complex: targeting of a protein chaperone by an antitumor agent," Cell 89: 239-50.

Tolentino et al. (1996) "Intravitreous injections of vascular endothelial growth factor produce retinal ischemia and microangiopathy in an adult primate," Ophthalmology 103(11): 1820-28.

Tolentino et al. (1996) "Vascular endothelial growth factor is sufficient to produce iris neovascularization and neovascular glaucoma in a non-human primate," Arch. Ophthalmol. 114(8): 964-70.

van Geel et al. (1996) "Vascular perfusion and hypoxic areas in RIF-1 tumours after photodynamic therapy," Br. J. Canc. 73(3): 288-93.

Wax et al. (2003) "Geldanamycin inhibits the production of inflammatory cytokines in activated macrophages by reducing the stability and translation of cytokine transcripts," Arthritis Rheum. 48(2): 541-50.

Zheng et al. (2004) "Post-ischemic inflammation: molecular mechanisms and therapeutic implications," Neurol. Res. 26(8): 884-92.

* cited by examiner

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: chemically synthesized

<400> SEQUENCE: 1

Ala Cys Asp Cys Arg Gly Asp Cys Phe Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: chemically synthesized

<400> SEQUENCE: 2

Lys Leu Ala Lys Leu Ala Lys Lys Leu Ala Lys Leu Ala Lys
1               5                   10

METHODS AND COMPOSITIONS FOR TREATING CONDITIONS OF THE EYE

CROSS-REFERENCE TO RELATED APPLICATION

The present application claims the benefit of and priority to U.S. patent application Ser. No. 60/773,890, filed Feb. 16, 2006, the entire disclosure of which is incorporated by reference herein for all purposes.

FIELD OF THE INVENTION

The invention relates generally to methods and compositions for treating ocular conditions and, more specifically, the invention relates to photodynamic therapy ("PDT")-based methods and compositions for treating ocular conditions characterized by unwanted choroidal neovasculature ("CNV").

BACKGROUND

Choroidal neovascularization can lead to hemorrhage and fibrosis, with resulting visual loss in a number of conditions of the eye, including, for example, age-related macular degeneration ("AMD"), ocular histoplasmosis syndrome, pathologic myopia, angioid streaks, idiopathic disorders, choroiditis, choroidal rupture, overlying choroid nevi, and certain inflammatory diseases. One of the disorders, namely, AMD, is the leading cause of severe vision loss in people aged 65 and above (Bressler et al. (1988) Surv. Ophthalmol. 32: 375-413; Guyer et al. (1986) Arch. Ophthalmol. 104: 702-705; Hyman et al. (1983) Am. J. Epidemiol. 188: 816-824; Klein & Klein (1982) Arch. Ophthalmol. 100: 571-573; Leibowitz et al. (1980) Surv. Ophthalmol. 24: 335-610). Age-related macular degeneration is the leading cause of legal blindness in individuals older than 50 years in the Western societies (Bressler et al. (1988) supra). Although clinicopathologic descriptions have been made, little is understood about the etiology and pathogenesis of the disease.

Dry AMD is the more common form of the disease, characterized by drusen, pigmentary and atrophic changes in the macula, with slowly progressive loss of central vision. Wet or neovascular AMD is characterized by subretinal hemorrhage, fibrosis and fluid secondary to the formation of CNV, and more rapid and pronounced loss of vision. While less common than dry AMD, neovascular AMD accounts for 80% of the severe vision loss due to AMD. Choroidal neovasculature in exudative (wet) AMD is responsible for the majority of severe vision loss (Freund et al. (1993) Am. J. Ophthalmol. 115(6):786-91). Approximately 200,000 cases of neovascular AMD are diagnosed yearly in the United States alone.

Currently, treatment of the dry form of AMD includes administration of antioxidant vitamins and/or zinc. Treatment of the wet form of AMD, however, has proved to be more difficult. Currently, there are a limited number of methods that have been approved in the United States of America for treating the wet form of AMD. These include laser photocoagulation, PDT using a benzoporphyrin derivative photosensitizer, and intravitreal injection of drugs such as pegaptanib (Macugen®) or ranibizumab (Lucentis®). Laser photocoagulation was until recently the only well-established and widely accepted treatment for CNV. However, it is beneficial only for a small subset of patients, has a high rate of CNV persistence and recurrence and results in iatrogenic, collateral damage to the overlying retina. During laser photocoagulation, thermal laser light is used to heat and photocoagulate the neovasculature of the choroid. A problem associated with this approach is that the laser light must pass through the photoreceptor cells of the retina in order to photocoagulate the blood vessels in the underlying choroid. As a result, this treatment destroys the photoreceptor cells of the retina creating blind spots with associated vision loss.

Another therapeutic modality that can attack CNV without significant collateral damage to the adjacent retina is PDT. Photodynamic therapy utilizes an intravascular photosensitizer that causes vessel occlusion by a non-thermal photochemical reaction (Miller et al. (1999) Arch. Ophthalmol. 117(9):1161-73; Zacks et al. (2002) Invest. Ophthalmol. Vis. Sci. 43(7): 2384-91). During PDT, a benzoporphyrin derivative photosensitizer is administered to the individual to be treated. Once the photosensitizer accumulates in the CNV, non-thermal light from a laser is applied to the region to be treated, which activates the photosensitizer in that region. The activated photosensitizer generates free radicals that damage the vasculature in the vicinity of the photosensitizer (see, U.S. Pat. Nos. 5,798,349 and 6,225,303). This approach is more selective than laser photocoagulation and is less likely to result in blind spots. Under certain circumstances, this treatment has been found to restore vision in patients afflicted with the disorder (see, U.S. Pat. Nos. 5,756,541 and 5,910,510).

During clinical studies, it has been found that recurrence of leakage appears in at least a portion of the CNV by one to three months post-treatment. Increasing photosensitizer or light doses do not appear to prevent this recurrence, and can even lead to undesired non-selective damage to retinal vessels (Miller et al. (1999) Archives of Ophthalmology 117: 1161-1173). Another avenue of investigation is to repeat the PDT procedure over prolonged periods of time. The necessity for repeated PDT treatments can nevertheless be expected to lead to cumulative damage to the retinal pigment epithelium ("RPE") and choriocapillaris, which may lead to progressive treatment-related vision loss. In addition, PDT can cause transient visual disturbances, injection-site adverse effects, transient photosensitivity reactions, infusion-related back pain, and vision loss. Photodynamic therapy represents a standard treatment for CNV, with variable effectiveness.

Therefore, there is still a need for improved methods for treating AMD characterized by unwanted CNV that increase the efficacy and selectivity of treatment, and which reduce or delay a recurrence of the disorder. There also is a need to improve neuroprotection in the retina overlying the CNV.

SUMMARY OF THE INVENTION

The present invention is directed to methods and compositions for treating ocular conditions associated with unwanted CNV. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases.

The invention, for example, provides a more effective PDT-based method for treating unwanted CNV, by, for example, decreasing or inhibiting PDT-induced upregulation of vascular endothelial growth factor; improving closure of lesions associated with PDT treatment; increasing efficacy of treatment; increasing selectivity for CNV; and/or reducing or delaying the recurrence of the condition following PDT.

Such effects when using a combination of photodynamic therapy and an additional agent, particularly those that improve closure of lesions following photodynamic therapy treatment or that increase endostatin levels, may be synergistic when compared with the effects of each of the photodynamic therapy and the additional agent alone. Moreover, because vascular endothelial growth factor may be involved in the formation of neovascular membranes and because photodynamic therapy can induce upregulation of vascular endothelial growth factor, treating this photodynamic therapy-induction of vascular endothelial growth factor with an additional agent in combination with photodynamic therapy may reduce or eliminate a secondary effect of photodynamic therapy that is counter-productive to effective treatment.

In one aspect, the invention provides a method of treating unwanted choroidal neovasculature in a mammal including the steps of (a) performing photodynamic therapy on the unwanted choroidal neovasculature and (b) administering to the mammal an ansamycin analog in an amount sufficient to decrease or inhibit photodynamic therapy-induced upregulation of vascular endothelial growth factor.

In another aspect, the invention provides a method of treating unwanted choroidal neovasculature in a mammal including the steps of (a) performing photodynamic therapy on the unwanted choroidal neovasculature and (b) administering to the mammal a heat shock protein 90 inhibitor in an amount sufficient to decrease or inhibit photodynamic therapy-induced upregulation of vascular endothelial growth factor.

Either aspect of the invention described above can have any of the following features. Step (b) can occur before, simultaneous with, or after, step (a). A mammal can be a primate, such as a human. Step (a) can include administering a photosensitizer to the mammal and irradiating the photosensitizer when disposed within the choroidal neovasculature.

In another aspect, the invention provides an improved photodynamic therapy-based method of treating unwanted choroidal neovasculature in a mammal, the improvement including administering to the mammal an ansamycin analog in an amount sufficient to mitigate a side effect associated with the photodynamic therapy.

In another aspect, the invention provides an improved photodynamic therapy-based method of treating unwanted choroidal neovasculature in a mammal, the improvement including administering to the mammal a heat shock protein 90 inhibitor in an amount sufficient to mitigate a side effect associated with the photodynamic therapy.

Either of the two aspects of the invention providing an improved photodynamic therapy method described immediately above can have any of the following features. The side effect can comprise photodynamic therapy-induced upregulation of vascular endothelial growth factor. Where the side effect includes upregulation of vascular endothelial growth factor, the method can mitigate the photodynamic therapy-induced upregulation of vascular endothelial growth factor by decreasing or inhibiting the photodynamic therapy-induced upregulation of vascular endothelial growth factor. The improved photodynamic therapy method can include using a benzoporphyrin derivative photosensitizer. The improved photodynamic therapy method can further include administering an effective amount of an anti-VEGF aptamer, an anti-VEGF antibody, and/or an anti-VEGF siRNA. The improved photodynamic therapy method can ameliorate the symptoms of age-related macular degeneration.

In another aspect, the invention provides a method of treating unwanted choroidal neovasculature in a mammal including the steps of administering to the mammal a compound selected from the group consisting of an ansamycin analog and a heat shock protein 90 inhibitor (and combinations thereof) in an amount sufficient to permit an effective amount to localize in the choroidal neovasculature, administering to the mammal an amount of photosensitizer sufficient to permit an effective amount to localize in the choroidal neovasculature, and irradiating the choroidal neovasculature with laser light such that the light is absorbed by the photosensitizer so as to occlude the choroidal neovasculature.

This aspect of the invention can have any of the following features. A mammal can be a primate, such as a human. The compound can be administered to the mammal prior to administration of the photosensitizer, together with administration of the photosensitizer, and/or after administration of the photosensitizer. The compound can be administered in an amount sufficient to decrease or inhibit photodynamic therapy-induced upregulation of vascular endothelial growth factor.

In those aspects of the invention that include an ansamycin analog, a variety of ansamycin analogs may be used in the invention. Useful ansamycin analogs include, for example, geldanamycin, 17-allylamino-17-demethoxygeldanamycin, 17-dimethylaminoethylamino-17-demethoxy-geldanamycin, rifamycin (for example, rifamycin W), rifampicin, rifampin, rifapentine, herbimycin A, naphthomycins B (for example, 30-chloronaphthomycin C) C and H, actamycin (for example, 30-hydroxynaphthomycin C), benzoxazinorifamycin, kendomycin, 19-allylaminoherbimycin A, ansamitocin, maytansines, tolypomycins, streptovaricins, and combinations thereof. In certain embodiments, 17-allylamino-17-demethoxygeldanamycin is used.

In those aspects of the invention that include a heat shock protein 90 inhibitor, a variety of heat shock protein 90 inhibitors can be used in the invention. Useful heat shock protein 90 inhibitors include, for example, geldanamycin, 17-allylamino-17-demethoxygeldanamycin, 17-dimethylaminoethylamino-17-demethoxy-geldanamycin, SNX-2112, CNF1010, CNF2024, Radicicol, IPI-504, and combinations thereof. In certain embodiments, the heat shock protein 90 inhibitor is 17-allylamino-17-demethoxygeldanamycin.

Additionally, a variety of photosensitizers can be used. Useful photosensitizers include, for example, amino acid derivatives, azo dyes, xanthene derivatives, chlorins, tetrapyrrole derivatives, phthalocyanines, and/or assorted other photosensitizers. In certain embodiments, lutetium texaphyrin, hematoporphyrins, benzoporphyrin derivatives, benzoporphyrins, and hematoporphyrin derivatives can be used.

The foregoing aspects and embodiments of the invention may be more fully understood by reference to the following figures, detailed description and claims.

DETAILED DESCRIPTION OF THE INVENTION

The invention relates to an improved method for treating ocular conditions characterized as having unwanted CNV. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases. The invention provides one or more of the following advantages: decreased or inhibited PDT-induced upregulation of vascular endothelial growth factor ("VEGF"); improved closure of lesions associated with PDT treatment; increased efficacy of treatment; increased selectivity for CNV; and/or reduced or delayed recurrence of the condition following PDT.

The invention is directed to an improved PDT-based method for treating unwanted target CNV. The method can include administration of a photosensitizer to a mammal in need of such treatment in an amount sufficient to permit an effective amount (i.e., an amount sufficient to facilitate PDT) of the photosensitizer to localize in the target CNV. After administration of the photosensitizer, the CNV then is irradiated with laser light under conditions such that the light is absorbed by the photosensitizer. The photosensitizer, when activated by the light, generates singlet oxygen and free radicals, for example, reactive oxygen species, that result in damage to surrounding tissue. For example, PDT-induced damage of endothelial cells results in platelet adhesion and degranulation, leading to stasis and aggregation of blood cells and vascular occlusion.

One drawback to PDT is the need for multiple re-treatments to achieve a reduction in vision loss intrinsic to the disease. It has been shown that PDT-induced upregulation of growth factors, such as VEGF, can potentially cause the persistent angiographic leakage that characterizes a PDT failure and necessitates further re-treatments (Ferrario et al. (2000) Cancer Res. 60:4066-4069). An increase in efficacy and/or selectivity of the PDT, and/or reduction or delay of recurrence of the CNV, can be achieved by administering an ansamycin analog or heat shock protein 90 ("Hsp90") inhibitor to the mammal prior to, concurrent with, or after administration of the PDT therapy and/or photosensitizer.

Geldanamycin ("GA"), a bezoquinone ansamycin antibiotic, is a natural inhibitor of Hsp90, a chaperone molecule, that interacts with a variety of intracellular client proteins to facilitate their proper folding, prevent misfolding, and preserve their three-dimensional conformation to a functionally competent state (Isaacs et al. (2003) Cancer Cell 3: 213-17). Through their inhibitory effects on Hsp90 activity, ansamycin analogs and Hsp90 inhibitors, such as GA, can affect several key growth factor-initiated signal transduction pathways, including suppression of cell surface receptors, induction of misfolding, and subsequent proteosomal degradation and depletion of crucial kinases and transcription factors (Goetz et al. (2003) Ann. Oncol. 14(8): 1169-76). A GA derivative, 17-allylamino-17-demethoxygeldanamycin ("17AAG"), has been associated with a favorable profile of transient side effects in phase I clinical trials in cancer patients and preliminary evidence is consistent with a potent anti-angiogenic and anti-tumor activity in vivo in a variety of solid tumors (Munster et al. (2001) Cancer Res. 61(7): 2945-52; Goetz et al. (2003) Ann. Oncol. 14(8): 1169-76), In a rat model of STZ-induced diabetes, the ansamycin analog and Hsp90 inhibitor, GA, reduced the expression of important mediators of the pathophysiological mechanisms of diabetic retinopathy, such as VEGF, and suppressed cardinal manifestations, including vascular leakage (Poulaki et al. (2004) Am. J. Pathol. 165(2): 457-69).

As mentioned, it has been observed that PDT induces upregulation of VEGF in ocular tissue. Accordingly, and without wishing to be bound to theory regarding the mechanism of action of ansamycin analogs or Hsp90 inhibitors in treatment of unwanted CNV, it may be that selective inhibition by an ansamycin analog or Hsp90 inhibitor of PDT-induced upregulation of VEGF has a beneficial effect in the treatment of unwanted CNV. As such, one aspect of the present invention provides a method of treating unwanted CNV in a mammal by performing PDT and administering an ansamycin analog or Hsp90 inhibitor in an amount sufficient to decrease or inhibit PDT-induced upregulation of VEGF.

In addition, the combination of an ansamycin analog or Hsp90 inhibitor with PDT can mitigate a side-effect of PDT treatment, such as, for example, vascular leakage (i.e. can facilitate vascular closure) or PDT-induced upregulation of VEGF. As such, another aspect of the present invention provides an improved method for treating ocular disorders, for example, AMD, characterized by unwanted CNV. The improved method comprises administering to a mammal a combination of PDT and an effective amount of an ansamycin analog or Hsp90 inhibitor (i.e., an amount sufficient to facilitate or enhance PDT) to mitigate a side effect associated with PDT. Furthermore, there is a synergistic effect of the administration of ansamycin analogs or Hsp90 inhibitors with PDT in treating CNV, and it may reduce the recurrence of CNV and increase the effectiveness of PDT. For example, administration of an ansamycin analog or Hsp90 inhibitor with PDT can synergistically enhance vascular closure in the eye or synergistically increase endostatin levels in the eye.

Numerous ansamycin analogs or Hsp90 inhibitors are well known and thoroughly documented in the art. An ansamycin analog is any compound or class of compounds that has a similar structure, function and/or mechanism of action to ansamycin or any ansamycin analog described herein. Ansamycin analogs can include, but are not limited to, proteins, peptides and derivatives thereof, including antibodies, antibody fragments, and antigen binding fragments; nucleic acids (such as DNAs, RNAs, and PNAs) and derivatives thereof, including antisense nucleic acids and siRNAs; and small organic and inorganic molecules. Examples of ansamycin analogs useful in the practice of the invention, include, for example, geldanamycin, 17-allylamino-17-demethoxygeldanamycin, 17-dimethylaminoethylamino-17-demethoxy-geldanamycin, rifamycin (for example, rifamycin W), rifampicin, rifampin, rifapentine, herbimycin A, naphthomycins B (for example, 30-chloronaphthomycin C) C and H, actamycin (for example, 30-hydroxynaphthomycin C), benzoxazinorifamycin, kendomycin, 19-allylaminoherbimycin A, ansamitocin, maytansines, tolypomycins, streptovaricins, and combinations thereof.

An Hsp90 inhibitor is any compound or class of compounds that inhibits the function of Hsp90 directly or indirectly, or that has a similar structure to such compounds or classes of compounds, and/or that has a similar structure, function and/or mechanism of action as the Hsp90 inhibitors described herein. Heat shock protein 90 inhibitors can include, but are not limited to, proteins, peptides and derivatives thereof, including antibodies, antibody fragments, and antigen binding fragments; nucleic acids (such as DNAs, RNAs, and PNAs) and derivatives thereof, including antisense nucleic acids and siRNAs; and small organic and inorganic molecules. Examples of Hsp90 inhibitors useful in the practice of the invention, include, for example, geldanamycin, 17-allylamino-17-demethoxygeldanamycin, 17-dimethylaminoethylamino-17-demethoxy-geldanamycin, SNX-2112, CNF 1010, CNF2024, Radicicol, IPI-504, and combinations thereof.

It is contemplated that a variety of photosensitizers useful in PDT may be useful in the practice of the invention and include, for example, amino acid derivatives, azo dyes, xanthene derivatives, chlorins, tetrapyrrole derivatives, phthalocyanines, and assorted other photo sensitizers.

Amino acid derivatives include, for example, 5-aminolevulinic acid (Berg et al. (1997) Photochem. Photobiol. 65: 403-409; El-Far et al. (1985) Cell. Biochem. Function 3: 115-119). Azo dyes, include, for example, Sudan I, Sudan II, Sudan III, Sudan IV, Sudan Black, Disperse Orange, Disperse Red, Oil Red O, Trypan Blue, Congo Red, β-carotene (Mosky et al. (1984) Exp. Res. 155: 389-396). Xanthene derivatives, include, for example, rose bengal.

Chlorins include, for example, lysyl chlorin p6 (Berg et al. (1997) supra) and etiobenzochlorin (Berg et al. (1997) supra), 5,10,15,20-tetra (m-hydroxyphenyl)chlorin (M-THPC), N-aspartyl chlorin e6 (Dougherty et al. (1998) J. Natl. Cancer Inst. 90: 889-905), and bacteriochlorin (Korbelik et al. (1992) J. Photochem. Photobiol. 12: 107-119).

Tetrapyrrole derivatives include, for example, lutetium texaphrin (Lu-Tex, PCI-0123) (Dougherty et al. (1998) supra; Young et al. (1996) Photochem. Photobiol. 63: 892-897); benzoporphyrin derivative (BPD) (U.S. Pat. Nos. 5,171,749, 5,214,036, 5,283,255, and 5,798,349, Jori et al. (1990) Lasers Med. Sci. 5, 115-120), benzoporphyrin derivative mono acid (BPD-MA) (U.S. Pat. Nos. 5,171,749, 5,214,036, 5,283,255, and 5,798,349; Berg et al. (1997) supra; Dougherty et al. (1998) supra), hematoporphyrin (Hp) (Jori et al. (1990) supra), hematoporphyrin derivatives (HpD) (Berg et al. (1997) supra; West et al. (1990) In. J. Radiat. Biol. 58: 145-156), porfimer sodium or Photofrin (PHP) (Berg et al. (1997) supra), Photofrin II (PII) (He et al. (1994) Photochem. Photobiol. 59: 468-473), protoporphyrin IX (PpIX) (Dougherty et al. (1998) supra; He et al. (1994) supra), meso-tetra (4-carboxyphenyl)porphine (TCPP) (Musser et al. (1982) Res. Commun. Chem. Pathol. Pharmacol. 2: 251-259), meso-tetra (4-sulfonatophenyl)porphine (TSPP) (Musser et al. (1982) supra), uroporphyrin I (UROP-I) (El-Far et al. (1985) Cell. Biochem. Function 3: 115-119), uroporphyrin III (UROP-III) (El-Far et al. (1985) supra), tin ethyl etiopurpurin (SnET2), (Dougherty et al. (1998) supra 90: 889-905) and 13,17-bis[1-carboxypropionyl]carbamoylethyl-8-etheny-2-hydroxy-3-hydroxyiminoethyliden e-2,7,12,18-tetranethyl 6 porphyrin sodium (ATX-S10(Na)) (Mori et al. (2000) Jpn. J. Cancer Res. 91: 753-759; Obana et al. (2000) Arch. Ophthalmol. 118: 650-658; Obana et al. (1999) Lasers Surg. Med. 24: 209-222).

Phthalocyanines include, for example, chloroaluminum phthalocyanine (AlPcCl) (Rerko et al. (1992) Photochem. Photobiol. 55, 75-80), aluminum phthalocyanine with 2-4 sulfonate groups (AlPcS2-4) (Berg et al. (1997) supra; Glassberg et al. (1991) Lasers Surg. Med. 11: 432-439), chloroaluminum sulfonated phthalocyanine (CASPc) (Roberts et al. (1991) J. Natl. Cancer Inst. 83: 18-32), phthalocyanine (PC) (Jori et al. (1990) supra), silicon phthalocyanine (Pc4) (He et al. (1998) Photochem. Photobiol. 67: 720-728; Jori et al. (1990) supra), magnesium phthalocyanine (Mg2+-PC) (Jori et al. (1990) supra), zinc phthalocyanine (ZnPC) (Berg et al. (1997) supra). Other photosensitizers include, for example, thionin, toluidine blue, neutral red and azure c.

However, useful photosensitizers, include, for example, Lutetium Texaphyrin (Lu-Tex), a new generation photosensitizer having favorable clinical properties including absorption at about 730 nm permitting deep tissue penetration and rapid clearance. Lu-Tex is available from Alcon Laboratories, Fort Worth, Tex. Other useful photosensitizers include benzoporhyrin and benzoporphyrin derivatives, for example, BPD-MA and BPD-DA, available from QLT Inc., Vancouver, Canada.

The photosensitizer preferably is formulated into a delivery system that delivers high concentrations of the photosensitizer to the CNV. Such formulations may include, for example, the combination of a photosensitizer with a carrier that delivers higher concentrations of the photosensitizer to CNV and/or coupling the photosensitizer to a specific binding ligand that binds preferentially to a specific cell surface component of the CNV.

In one embodiment, the photosensitizer can be combined with a lipid based carrier. For example, liposomal formulations have been found to be particularly effective at delivering the photosensitizer, green porphyrin, and more particularly BPD-MA to the low-density lipoprotein component of plasma, which in turn acts as a carrier to deliver the photosensitizer more effectively to the CNV. Increased numbers of LDL receptors have been shown to be associated with CNV, and by increasing the partitioning of the photosensitizer into the lipoprotein phase of the blood, it may be delivered more efficiently to the CNV. Certain photosensitizers, for example, green porphyrins, and in particular BPD-MA, interact strongly with lipoproteins. LDL itself can be used as a carrier, but LDL is more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins formulated as lipocomplexes, including liposomes, are described, for example, in U.S. Pat. Nos. 5,214,036, 5,707, 608 and 5,798,349. Liposomal formulations of green porphyrin can be obtained from QLT Inc., Vancouver, Canada. It is contemplated that certain other photosensitizers may likewise be formulated with lipid carriers, for example, liposomes or LDL, to deliver the photosensitizer to CNV.

Furthermore, the photosensitizer can be coupled or conjugated to a targeting molecule that targets the photosensitizer to CNV. For example, the photosensitizer may be coupled or conjugated to a specific binding ligand that binds preferentially to a cell surface component of the CNV, for example, neovascular endothelial homing motif. It appears that a variety of cell surface ligands are expressed at higher levels in new blood vessels relative to other cells or tissues.

Endothelial cells in new blood vessels express several proteins that are absent or barely detectable in established blood vessels (Folkman (1995) Nature Medicine 1: 27-31), and include integrins (Brooks et al. (1994) Science 264: 569-571; Friedlander et al. (1995) Science 270: 1500-1502) and receptors for certain angiogenic factors like vascular endothelial growth factor VEGF. In vivo selection of phage peptide libraries have also identified peptides expressed by the vasculature that are organ-specific, implying that many tissues have vascular "addresses" (Pasqualini et al. (1996) Nature 380: 364-366). It is contemplated that a suitable targeting moiety can direct a photosensitizer to the CNV endothelium thereby increasing the efficacy and lowering the toxicity of PDT.

Several targeting molecules may be used to target photosensitizers to the neovascular endothelium. For example, α-v integrins, in particular α-v β3 and α-v β5, appear to be expressed in ocular neovascular tissue, in both clinical specimens and experimental models (Corjay et al. (1997) Invest. Ophthalmol. Vis. Sci. 38: S965; Friedlander et al. (1995) supra). Accordingly, molecules that preferentially bind α-v integrins can be used to target the photosensitizer to CNV. For example, cyclic peptide antagonists of these integrins have been used to inhibit neovascularization in experimental models (Friedlander et al. (1996) Proc. Natl. Acad. Sci. USA 93: 9764-9769). A peptide motif having an amino acid sequence, in an N- to C-terminal direction, ACDCRGDCFC (SEQ ID NO: 1)—also known as RGD-4C—has been identified that selectively binds to human α-v integrins and accumulates in tumor neovasculature more effectively than other angiogenesis targeting peptides (Arap et al. (1998) Nature 279: 377-380; Ellerby et al. (1999) Nature Medicine 5: 1032-1038). Angiostatin may also be used as a targeting molecule for the photosensitizer. Studies have shown, for example, that angiostatin binds specifically to ATP synthase disposed on the surface of human endothelial cells (Moser et al. (1999) Proc. Natl. Acad. Sci. USA 96: 2811-2816).

Clinical and experimental evidence strongly supports a role for VEGF in ocular neovascularization, particularly ischemia-associated neovascularization (Adamis et al. (1996) Arch. Ophthalmol. 114:66-71; Tolentino et al. (1996) Arch. Ophthalmol. 114:964-970; Tolentino et al. (1996) Ophthalmology 103:1820-1828). Potential targeting molecules include antibodies that bind specifically to either VEGF or the VEGF receptor (VEGF-2R). Antibodies to the VEGF receptor (VEGFR-2 also known as KDR) may also bind preferentially to neovascular endothelium.

The targeting molecule may be synthesized using methodologies known and used in the art. For example, proteins and peptides may be synthesized using conventional synthetic peptide chemistries or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press. Once created, the targeting agent may be coupled or conjugated to the photosensitizer using standard coupling chemistries, using, for example, conventional cross linking reagents, for example, heterobifunctional cross linking reagents available, for example, from Pierce, Rockford, Ill.

Once formulated, the photosensitizer may be administered in any of a wide variety of ways, for example, orally, parenterally, or rectally. Parenteral administration, such as intravenous, intramuscular, or subcutaneous, is preferred. Intravenous injection is especially preferred. The dose of photosensitizer can vary widely depending on the tissue to be treated; the physical delivery system in which it is carried, such as in the form of liposomes; or whether it is coupled to a target-specific ligand, such as an antibody or an immunologically active fragment.

It should be noted that the various parameters used for effective, selective PDT in the invention are interrelated. Therefore, the dose should also be adjusted with respect to other parameters, for example, fluence, irradiance, duration of the light used in PDT, and time interval between administration of the dose and the therapeutic irradiation. All of these parameters should be adjusted to produce significant damage to CNV without significant damage to the surrounding tissue.

Typically, the dose of photosensitizer used is within the range of from about 0.1 to about 20 mg/kg, preferably from about 0.15 to about 5.0 mg/kg, and even more preferably from about 0.25 to about 2.0 mg/kg. Furthermore, as the dosage of photosensitizer is reduced, for example, from about 2 to about 1 mg/kg in the case of green porphyrin or BPD-MA, the fluence required to close CNV may increase, for example, from about 50 to about 100 Joules/cm$^2$. Similar trends may be observed with the other photosensitizers discussed herein.

After the photosensitizer has been administered, the CNV is irradiated at a wavelength typically around the maximum absorbance of the photosensitizer, usually in the range from about 550 nm to about 750 nm. A wavelength in this range is especially preferred for enhanced penetration into bodily tissues. Preferred wavelengths used for certain photosensitizers include, for example, about 690 nm for benzoporphyrin derivative mono acid, about 630 run for hematoporphyrin derivative, about 675 nm for chloro-aluminum sulfonated phthalocyanine, about 660 nm for tin ethyl etiopurpurin, about 730 nm for lutetium texaphyrin, about 670 nm for ATX-S 10(NA), about 665 nm for N-aspartyl chlorin e6, and about 650 nm for 5,10,15,20-tetra (m-hydroxyphenyl)chlorin.

As a result of being irradiated, the photosensitizer in its triplet state is thought to interact with oxygen and other compounds to form reactive intermediates, such as singlet oxygen and reactive oxygen species, which can disrupt cellular structures. Possible cellular targets include the cell membrane, mitochondria, lysosomal membranes, and the nucleus. Evidence from tumor and neovascular models indicates that occlusion of the vasculature is a major mechanism of PDT, which occurs by damage to the endothelial cells, with subsequent platelet adhesion, degranulation, and thrombus formation.

The fluence during the irradiating treatment can vary widely, depending on the type of photosensitizer used, the type of tissue, the depth of target tissue, and the amount of overlying fluid or blood. Fluences preferably vary from about 10 to about 400 Joules/cm$^2$ and more preferably vary from about 50 to about 200 Joules/cm$^2$, The irradiance varies typically from about 50 mW/cm$^2$ to about 1800 mW/cm$^2$, more preferably from about 100 mW/cm$^2$ to about 900 mW/cm$^2$, and most preferably in the range from about 150 mW/cm$^2$ to about 600 mW/cm$^2$, It is contemplated that for many practical applications, the irradiance will be within the range of about 300 mW/cm$^2$ to about 900 mW/cm$^2$, However, the use of higher irradiances may be selected as effective and having the advantage of shortening treatment times.

The time of light irradiation after administration of the photosensitizer may be important as one way of maximizing the selectivity of the treatment, thus minimizing damage to structures other than the target tissues. The optimum time following photosensitizer administration until light treatment can vary widely depending on the mode of administration, the form of administration such as in the form of liposomes or as a complex with LDL, and the type of target tissue. For example, benzoporphyrin derivative typically becomes present within the target neovasculature within one minute post administration and persists for about fifty minutes, lutetium texaphyrin typically becomes present within the target neovasculature within one minute post administration and persists for about twenty minutes, N-aspartyl chlorin e6 typically becomes present within the target neovasculature within one minute post administration and persists for about twenty minutes, and rose bengal typically becomes present in the target vasculature within one minute post administration and persists for about ten minutes.

Effective vascular closure generally occurs at times in the range of about one minute to about three hours following administration of the photosensitizer. However, as with green porphyrins, it is undesirable to perform the PDT within the first five minutes following administration to prevent undue damage to retinal vessels still containing relatively high concentrations of photosensitizer.

The efficacy of PDT may be monitored using conventional methodologies, for example, via fundus photography or angiography, such as fluorescein angiography. Closure can usually be observed angiographically by hypofluorescence in the treated areas in the early angiographic frames. During the later angiographic frames, a corona of hyperfluorescence may begin to appear which then fills the treated area, possibly representing leakage from the adjacent choriocapillaris through damaged retinal pigment epithelium in the treated area. Large retinal vessels in the treated area typically perfuse following PDT.

Minimal retinal damage is generally found on histopathologic correlation and is dependent on the fluence and the time interval after irradiation that the photosensitizer is administered. It is contemplated that the choice of appropriate photosensitizer, dosage, mode of administration, formulation, timing post administration prior to irradiation, and irradiation parameters may be determined empirically.

It is contemplated that a variety of ansamycin analogs or Hsp90 inhibitors may be combined with other treatments for treating unwanted CNV. The ansamycin analogs or Hsp90 inhibitors can synergistically enhance the activity of the treatment, for example, PDT. In addition, the ansamycin analogs or Hsp90 inhibitors can be used to reduce or delay the recurrence of the condition. An ansamycin analog or Hsp90 inhibitor is understood to mean any molecule, for example, a protein, peptide, nucleic acid (ribonucleic acid (RNA) or deoxyribonucleic acid (DNA)), peptidyl nucleic acid, organic compound or inorganic compound having one or more of the activities described herein. An effective amount of an ansamycin analog or Hsp90 inhibitor is an amount sufficient to treat or enhance treatment of unwanted CNV. The combination treatment of an ansamycin analog or Hsp90 inhibitor and PDT also can include other factors that target VEGF. For example, the ansamycin analog or Hsp90 inhibitor may be combined with an anti-VEGF aptamer, for example the Macugene®aptamer (see the URL address eyetk.com/science/science_vegf.asp), for treatment of AMD (available from Eyetech Pharmaceuticals, Inc., NY, N.Y.). Alternatively, the ansamycin analog or Hsp90 inhibitor may be combined with a VEGF specific RNAi for the treatment of AMD (see the URL address: alnylam.com/therapeutic-programs/programs.asp) (available from Alnylam Pharmaceuticals, Cambridge, Mass.). Similarly, the ansamycin analog or Hsp90 inhibitor may be combined with an anti-VEGF antibody or antibody fragment for the treatment of AMD (see the URL address: gene.com/gene/products/information/oncology/avastin/index.jps) (available from Genentech, Inc., San Francisco, Calif.).

The combination treatment of an ansamycin analog or Hsp90 inhibitor and PDT could also include, for example, one or a combination of anti-angiogenesis factors. The term "anti-angiogenesis factor" is understood to mean any molecule, for example, a protein, peptide, nucleic acid (ribonucleic acid (RNA) or deoxyribonucleic acid (DNA)), peptidyl nucleic acid, organic compound or inorganic compound, that reduces or inhibits the formation of new blood vessels in a mammal. It is contemplated that useful angiogenesis inhibitors, if not already known, may be identified using a variety of assays well known and used in the art. Such assays include, for example, the bovine capillary endothelial cell proliferation assay, the chick chorioallantoic membrane (CAM) assay or the mouse corneal assay. However, the CAM assay is preferred (see, for example, O'Reilly et al. (1994) Cell 79: 315-328 and O'Reilly et al. (1997) Cell 88: 277-285). Briefly, embryos with intact yolks are removed from fertilized three day old white eggs and placed in a petri dish. After incubation at 37° C., 3% $CO_2$ for three days, a methylcellulose disk containing the putative angiogenesis inhibitor is applied to the chorioallantoic membrane of an individual embryo. After incubation for about 48 hours, the chorioallantoic membranes are observed under a microscope for evidence of zones of inhibition.

Numerous anti-angiogenesis factors are well known and thoroughly documented in the art (see, for example, PCT/US99/08335). Examples of anti-angiogenesis factors useful in the practice of the invention, include, for example, protein/peptide inhibitors of angiogenesis such as: angiostatin, a proteolytic fragment of plasminogen (O'Reilly et al. (1994) Cell 79: 315-328, and U.S. Pat. Nos. 5,733,876; 5,837,682; and 5,885,795) including full length amino acid sequences of angiostatin, bioactive fragments thereof, and analogs thereof; endostatin, a proteolytic fragment of collagen XVIII (O'Reilly et al. (1997) Cell 88: 277-285; Cirri et al. (1999) Int. Biol. Marker 14: 263-267, and U.S. Pat. No. 5,854,205) including full length amino acid sequences of endostatin, bioactive fragments thereof, and analogs thereof; peptides containing the RGD tripeptide sequence and capable of binding the $\alpha_v\beta_3$ integrin (Brooks et al. (1994) Cell 79: 1157-1164; Brooks et al. (1994) Science 264: 569-571); certain antibodies and antigen binding fragments thereof and peptides that bind preferentially to the $\alpha_v\beta_3$ integrin found on tumor vascular epithelial cells (Brooks et al., supra; Friedlander et al. (1996) Proc. Natl. acad. Sci. USA 93: 9764-9769); certain antibodies and antigen binding fragments thereof and peptides that bind preferentially to the epidermal growth factor receptor (Ciardello et al. (1996) J. Natl. Cancer Inst. 88: 1770-1776, Ciardello et al. (2000) Clin. Cancer Res. 6:3739-3747); antibodies, proteins, peptides and/or nucleic acids that bind preferentially to and neutralize VEGF (Adamis et al. (1996) Arch. Opthalmol. 114: 66-71), antibodies, proteins, and/or peptides that bind preferentially to and neutralize VEGF receptor; anti-fibroblast growth factor, anti-epidermal growth factor (Ciardiello et al. (2000) Clin. Cancer Res. 6: 3739-3747) including full length amino acid sequences, bioactive fragments and analogs thereof, and pigment epithelium-derived growth factor (Dawson (1999) Science 2035: 245-248) including full length amino acid sequences, bioactive fragments and analogs thereof. Bioactive fragments refer to portions of the intact protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

Other angiogenesis inhibitors include, for example: COX-2 selective inhibitors (Masferrer et al. (1998) Proc. Amer. Assoc. Cancer Res. 39: 271; Ershov et al. (1999) J. Neurosci. Res. 15: 254-261; Masferrer et al. (2000) Curr. Med. Chem. 7: 1163-1170); tyrosine kinase inhibitors, for example, PD 173074 (Dimitroff et al. (1999) Invest. New Drugs 17: 121-135), halofuginone (Abramovitch et al. (1999) Neoplasia 1: 321-329; Elkin et al. (1999) Cancer Res. 5: 1982-1988), AGM-1470 (Brem et al. (1993) J. Ped. Surgery 28: 1253-1257), angiogenic steroids, for example, hydrocortisone and anecortave acetate (Penn et al. (2000) Invest. Opthalmol. Vis. Sci. 42: 283-290), thrombospondin-1 (Shafiee et al. (2000) Invest. Ophthalmol. Vis. Sci. 8: 2378-2388; Nor et al. (2000) J. Vasc. Res. 37: 09-218), UCN-01 (Kruger et al. (1998-1999) Invasion Metastasis 18: 209-218), CM101 (Sundell et al. (1997) Clin. Cancer Res. 3: 365-372); fumagillin and analogues such as AGM-1470 (Ingber et al. (1990) Nature 348: 555-557), and other small molecules such as thalidomide (D'Amato et al. (1994) Proc. Natl. Acad. Sci. USA 91: 4082-4085).

Several cytokines including bioactive fragments thereof and analogs thereof have also been reported to have anti-angiogenic activity and thus can be useful in the practice of the invention. Examples include, for example, IL-12, which reportedly works through an IFN-γ-dependent mechanism (Voest et al. (1995) J. Natl. Canc. Inst. 87: 581-586); IFN-α, which has been shown to be anti-angiogenic alone or in combination with other inhibitors (Brem et al. (1993) J. Pediatr. Surg. 28: 1253-1257). Furthermore, the interferons IFN-α, IFN-β and IFN-γ reportedly have immunological effects, as well as anti-angiogenic properties, that are independent of their anti-viral activities. However, preferred anti-angiogenic factors include endostatin and angiostatin.

Ansamycin analogs, Hsp90 inhibitors, and/or other factors (e.g. angiogenesis inhibitors) may be synthesized using methodologies known and used in the art. For example, proteins and peptides may be synthesized and purified using conventional synthetic peptide chemistries and purification protocols, or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press.

To the extent that the ansamycin analog, Hsp90 inhibitor, and/or other factor is a nucleic acid or peptidyl nucleic acid, such compounds may be synthesized by any of the known chemical oligonucleotide and peptidyl nucleic acid synthesis methodologies known in the art (see, for example, PCT/EP92/20702 and PCT/US94/013523) and used in antisense therapy. Anti-sense oligonucleotide and peptidyl nucleic acid sequences, usually 10 to 100 and more preferably 15 to 50 units in length, are capable of hybridizing to a gene and/or mRNA transcript and, therefore, may be used to inhibit transcription and/or translation of a target protein. It is appreciated, however, that oligoribonucleotide sequences generally are more susceptible to enzymatic attack by ribonucleases than are deoxyribonucleotide sequences. Hence, oligodeoxyribonucleotides are preferred over oligoribonucleotides for in vivo use. In the case of nucleotide sequences, phosphodiester linkages may be replaced by thioester linkages making the resulting molecules more resistant to nuclease degradation. Furthermore, it is appreciated that the peptidyl nucleic acid sequences, unlike regular nucleic acid sequences, are not susceptible to nuclease degradation and, therefore, are likely to have greater longevity in vivo. Furthermore, it has been found that peptidyl nucleic acid sequences bind complementary single stranded DNA and RNA strands more strongly than corresponding DNA sequences (PCT/EP92/20702). Furthermore, to the extent that the ansamycin analog, Hsp90 inhibitor, and/or other factor is an organic or inorganic compound, such compounds may be synthesized, extracted and/or purified by standard procedures known in the art. To the extent RNAi is used, double stranded RNA (dsRNA) having one strand identical (or substantially identical) to the target mRNA sequence is introduced to a cell. The dsRNA is cleaved into small interfering RNAs (siRNAs) in the cell, and the siRNAs interact with the RNA induced silencing complex to degrade the target mRNA, ultimately destroying production of a desired protein. Alternatively, siRNA may be introduced directly into the cell.

The type and amount of ansamycin analog, Hsp90 inhibitor, and/or other factor to be administered may depend upon the PDT and cell type to be treated. It is contemplated, however, that optimal modes of administration and dosages may be determined empirically. The ansamycin analog, Hsp90 inhibitor, and/or other factor may be administered in a pharmaceutically acceptable carrier or vehicle so that administration does not otherwise adversely affect the recipient's electrolyte and/or volume balance. The carrier may comprise, for example, physiologic saline.

By way of example, ansamycin analogs, Hsp90 inhibitors, and/or other factors, alone or in combination, can be administered at doses ranging, for example, from about 0.001 to about 500 mg/kg, optionally from about 0.01 to about 250 mg/kg, and optionally from about 0.1 to about 100 mg/kg. Nucleic acid-based ansamycin analogs, Hsp90 inhibitors and/or other factors may be administered at doses ranging from about 1 to about 20 mg/kg periodically, for example, daily. Furthermore, antibodies that are ansamycin analogs, Hsp90 inhibitors and/or other factors may be administered at doses ranging from about 0.1 to about 5 mg/kg periodically, for example, by intravenous delivery once every two to four weeks. With regard to intravitreal administration, the ansamycin analog, Hsp90 inhibitor and/or other factor, for example, an antibody or other composition, may be administered periodically as a bolus at dosages ranging from about 10 μg to about 5 mg/eye, and optionally from about 100 μg to about 2 mg/eye. With regard to transcleral administration, the ansamycin analog, Hsp90 inhibitor and/or other factor may be administered periodically as a bolus at dosages ranging from about 0.1 μg to about 1 mg/eye, and optionally from about 0.5 μg to about 0.5 mg/eye. With regard to intraperitoneal administration, the ansamycin analog, Hsp90 inhibitor and/or other factor can be administered at dosages ranging from about 0.001 to about 500 mg/kg, and optionally from about 0.1 to about 100 mg/kg.

The ansamycin analog, Hsp90 inhibitor, and/or other factor can be administered to the mammal prior to PDT, although it may alternatively or additionally be administered during and/or after PDT. Accordingly, they can be administered prior to, together with, and/or after administration of the photosensitizer. The ansamycin analog, Hsp90 inhibitor, and/or other factor, as well as the photosensitizer, may be administered in any one of a wide variety of ways, for example, orally, parenterally, intraperitoneally, or rectally. Parenteral administration includes intravenous, intramuscular, subcutaneous, subtenons, transcleral, and intravitreal administration. Administration may be provided as a periodic bolus (for example, intravenously or intravitreally) or as continuous infusion from an internal reservoir (for example, from a bioerodable implant disposed at an intra- or extra-ocular location) or from an external reservoir (for example, from an intravenous bag). The ansamycin analog, Hsp90 inhibitor, and/or other factor may be administered locally, for example, by continuous release from a sustained release drug delivery device immobilized to an inner wall of the eye or via targeted trans-scleral controlled release into the choroid (see, PCT/US00/00207), or the ansamycin analog, Hsp90 inhibitor, and/or other factor may be administered systemically. Additionally, the ansamycin analog, Hsp90 inhibitor, and/or other factor can be administered as an ointment, encapsulated in microspheres or liposomes, or placed in a device for longer release.

The present invention, therefore, includes the use of an ansamycin analog, Hsp90 inhibitor, and/or other factor in the preparation of a medicament for treating, preferably by a PDT-based method, an ocular condition, that preferably is associated with CNV. The ansamycin analog, Hsp90 inhibitor, and/or other factor may be provided in a kit which optionally may comprise a package insert with instructions for how to treat such a condition. A composition comprising both a photosensitizer and an ansamycin analog, Hsp90 inhibitor, and/or other factor may be provided for use in the present invention. The composition may comprise a pharmaceutically acceptable carrier or excipient. Thus, the present invention includes a pharmaceutically acceptable composition comprising a photosensitizer and an ansamycin analog, Hsp90 inhibitor, and/or other factor; as well as the composition for use in medicine. More preferably, however, the invention is for use in combination therapy, whereby an ansamycin analog, Hsp90 inhibitor, and/or other factor and a photosensitizer are administered separately. The ansamycin analog, Hsp90 inhibitor, and/or other factor can be administered prior to, with, or after administration of the photosensitizer. Instructions for such administration may be provided with the ansarnycin analog, Hsp90 inhibitor, and/or other factor and/or with the photosensitizer. If desired, the ansamycin analog, Hsp90 inhibitor, other factor, and/or photosensitizer may be provided together in a kit, optionally including a package insert with instructions for use. The ansamycin analog, Hsp90 inhibitor, and/or other factor and photosensitizer preferably are provided in separate containers. For each administration, the ansamycin analog, Hsp90 inhibitor, and/or other factor and/or photosensitizer may be provided in unit-dosage or multiple-dosage form. Preferred dosages of photosensitizer and ansamycin analog, Hsp90 inhibitor, and/or other factor, however, are as described above.

It is also contemplated that the combination treatment of an ansamycin analog or Hsp90 inhibitor and PDT, which can mitigate a side effect of PDT, with or without other factors described above, can also include an apoptosis-modulating factor. An apoptosis-modulating factor can be any factor, for example, a protein (for example a growth factor or antibody), peptide, nucleic acid (for example, an antisense oligonucleotide), peptidyl nucleic acid (for example, an antisense molecule), organic molecule or inorganic molecule, that induces or represses apoptosis in a particular cell type. For example, it may be advantageous to prime the apoptotic machinery of CNV endothelial cells with an inducer of apoptosis prior to PDT so as to increase their sensitivity to PDT. Endothelial cells primed in this manner are contemplated to be more susceptible to PDT. This approach may also reduce the light dose (fluence) required to achieve CNV closure and thereby decrease the level of damage on surrounding cells such as RPE. Alternatively, the cells outside the CNV may be primed with an a repressor of apoptosis so as to decrease their sensitivity to PDT. In this approach, the PDT at a particular fluence can become more selective for CNV.

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) Br. J. Cancer 26: 239-257). At the core of this process lies a conserved set of proenzymes, called caspases, and two important members of this family are caspases 3 and 7 (Nicholson et al. (1997) TIBS 22: 299-306). Monitoring their activity can be used to assess on-going apoptosis.

It has been suggested that apoptosis is associated with the generation of reactive oxygen species, and that the product of the Bcl-2 gene protects cells against apoptosis by inhibiting the generation or the action of the reactive oxygen species (Hockenbery et al. (1993) Cell 75: 241-251; Kane et al. (1993) Science 262: 1274-1277; Veis et al. (1993) Cell 75: 229-240, Virgili et al. (1998) Free Radicals Biol. Med. 24: 93-101). Bcl-2 belongs to a growing family of apoptosis regulatory gene products, which may either be death antagonists (Bcl-2, Bcl-xL) or death agonists (Bax, Bak) (Kroemer et al. (1997) Nat. Med. 3: 614-620). Control of cell death appears to be regulated by these interactions and by constitutive activities of the various family members (Hockenbery et al. (1993) Cell 75: 241-251). Several apoptotic pathways may coexist in mammalian cells that are preferentially activated in a stimulus-, stage-, context-specific and cell-type manner (Hakem et al. (1998) Cell 94: 339-352).

The apoptosis-inducing factor preferably is a protein or peptide capable of inducing apoptosis in cells for example, endothelial cells, disposed in the CNV. One apoptosis inducing peptide comprises an amino sequence having, in an N- to C-terminal direction, KLAKLAKKLAKLAK (SEQ ID NO: 2). This peptide reportedly is non-toxic outside cells, but becomes toxic when internalized into targeted cells by disrupting mitochondrial membranes (Ellerby et al. (1999) supra). This sequence may be coupled, either by means of a crosslinking agent or a peptide bond, to a targeting domain, for example, the amino acid sequence known as RGD-4C (Ellerby et al. (1999) supra) that reportedly can direct the apoptosis-inducing peptide to endothelial cells. Other apoptosis-inducing factors include, for example, constatin (Kamphaus et al. (2000) J. Biol. Chem. 14: 1209-1215), tissue necrosis factor cc (Lucas et al. (1998) Blood 92: 4730-4741) including bioactive fragments and analogs thereof, cyclohex-imide (O'Connor et al. (2000) Am. J. Pathol. 156: 393-398), tunicamycin (Martinez et al. (2000) Adv. Exp. Med. Biol. 476: 197-208), and adenosine (Harrington et al. (2000) Am. J. Physiol. Lung Cell Mol. Physiol. 279: 733-742). Furthermore, other apoptosis-inducing factors may include, for example, anti-sense nucleic acid or peptidyl nucleic acid sequences that reduce or turn off the expression of one or more of the death antagonists, for example (Bcl-2, Bcl-xL). Antisense nucleotides directed against Bcl-2 have been shown to reduce the expression of Bcl-2 protein in certain lines together with increased phototoxicity and susceptibility to apoptosis during PDT (Zhang et al. (1999) Photochem. Photobiol. 69: 582-586). Furthermore, an 18mer phosphorothiate oligonucleotide complementary to the first six codons of the Bcl-2 open reading frame, and known as G3139, is being tested in humans as a treatment for non-Hodgkins' lymphoma.

Apoptosis-repressing factors include survivin, including bioactive fragments and analogs thereof (Papapetropoulos et al. (2000) J. Biol. Chem. 275: 9102-9105), CD39 (Goepfert et al. (2000) Mol. Med. 6: 591-603), BDNF (Caffe et al. (2001) Invest. Ophthalmol. Vis. Sci. 42: 275-82), FGF2 (Bryckaert et al. (1999) Oncogene 18: 7584-7593), Caspase inhibitors (Ekert et al. (1999) Cell Death Differ 6: 1081-1068) and pigment epithelium-derived growth factor including bioactive fragments and analogs thereof. Furthermore, other apoptosis-repressing factors may include, for example, anti-sense nucleic acid or peptidyl nucleic acid sequences that reduce or turn off the expression of one or more of the death agonists, for example (Bax, Bak).

To the extent that the apoptosis-modulating factor is a protein or peptide, nucleic acid, peptidyl nucleic acid, or organic or inorganic compound, it may be synthesized and purified by one or more the methodologies described relating to the synthesis of the ansamycin analog, Hsp90 inhibitor, and/or other factor.

The type and amount of apoptosis-modulating factor to be administered may depend upon the PDT and cell type to be treated. It is contemplated, however, that optimal apoptosis-modulating factors, modes of administration and dosages may be determined empirically. The apoptosis modulating factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based apoptosis modulators can be administered at doses ranging, for example, from about 0.001 to about 500 mg/kg, more preferably from about 0.01 to about 250 mg/kg, and most preferably from about 0.1 to about 100 mg/kg. For example, nucleic acid-based apoptosis inducers, for example, G318, may be administered at doses ranging from about 1 to about 20 mg/kg daily. Furthermore, antibodies may be administered intravenously at doses ranging from about 0.1 to about 5 mg/kg once every two to four weeks. With regard to intravitreal administration, the apoptosis modulators, for example, antibodies, may be administered periodically as bolus dosages ranging from about 10 µg to about 5 mg/eye and more preferably from about 100 µg to about 2 mg/eye.

The apoptosis-modulating factor preferably is administered to the mammal prior to PDT. Accordingly, it is preferable to administer the apoptosis-modulating factor prior to administration of the photosensitizer. The apoptosis-modulating factor, like the photosensitizer, ansamycin analog, Hsp90 inhibitor, and/or other factor, may be administered in any one of a wide variety of ways, for example, orally, parenterally, or rectally. However, parenteral administration, such as intravenous, intramuscular, subcutaneous, and intravitreal is preferred. Administration may be provided as a periodic bolus (for example, intravenously or intravitreally) or by continuous infusion from an internal reservoir (for example, bioerodable implant disposed at an intra- or extra-ocular location) or an external reservoir (for example, and intravenous bag). The apoptosis modulating factor may be administered locally, for example, by continuous release from a sustained release drug delivery device immobilized to an inner wall of the eye or via targeted trans-scleral controlled release into the choroid (see, PCT/US00/00207).

Although the foregoing methods and compositions of the invention may be useful in treat unwanted CNV and thereby ameliorate the symptoms of ocular disorders including, for example, AMD, ocular histoplasmosis syndrome, pathologic myopia, angioid streaks, idiopathic disorders, choroiditis, choroidal rupture, overlying choroid nevi, and inflammatory diseases, it is contemplated that the same methods and compositions may also be useful in treating other forms of ocular neovasculature. More specifically, the methods and compositions of the invention may likewise be useful at treating and removing or reducing corneal neovasculature, iris neovasculature, retinal neovasculature, retinal angiomas and choroidal hemangiomas.

The invention is illustrated further by reference to the following non-limiting example.

EXAMPLE 17-allylamino-17-demethoxygeldanamycin Treatment Reduces Choroidal Neovascularization Heat shock protein 90 ("Hsp90") is the central component of a ubiquitous molecular chaperone complex that interacts with a variety of intracellular client proteins to facilitate their proper folding, prevent misfolding or aggregation, and preserve their three-dimensional conformation to a functionally competent state. Heat shock protein 90 inhibitors, such as geldanamycin ("GA"), 17-allylamino-17-demethoxygeldanamycin ("17AAG") and other members of the ansamycin family, constitute promising investigational agents, as they have been recently shown to exhibit antitumor activity in a variety of models. To investigate the anti-angiogenic effects of 17AAG in a rat model of laser-induced CNV, the following experiment was undertaken.

Briefly, CNV membranes were induced in Brown-Norway rats using an Argon/Dye laser while either 17AAG at a total dose of approximately 2 mg or the vehicle (DMSO) was continuously administered. Verterporfin PDT was performed 14 days after CNV induction at a verterporfin dose of 3 mg/m$^2$, an irradiance of 600 mW/cm$^2$, and a fluence of 25 J/cm$^2$. Choroidal neovasculature closure on fluorescein angiograms was assessed 24 hours and 7 days after PDT in a masked fashion using grading standards. Retinal levels of p42/44 MAPK, HIF-1a, NF-kB, VEGF, and endostatin were assessed with a modified enzyme-linked immunoabsorbant assay ("ELISA") method. Results showed that administration of 17AAG increased the efficacy of verteporfin PDT on CNV closure. 17-allylamino-17-demethoxygeldanamycin treatment decreased the PDT-induced upregulation of p42/44 MAPK, HIF-1a and NF-kB activation and the PDT-induced upregulation of VEGF protein levels. The combination of 17-allylamino-17-demethoxygeldanamycin treatment and PDT treatment was also synergistic with respect to increased endostatin levels.

Materials and Methods
Induction of Choroidal Neovascularization

All experiments adhered to the Association for Research in Vision and Ophthalmology Statement for the Use of Animals in Ophthalmic and Vision Research and the guidelines established by the Animal Care Committee of the Massachusetts Eye and Ear Infirmary. Brown Norway rats (Charles River Laboratory, Wilmington, Mass.) were anesthetized via an intramuscular injection of 50 mg/kg of ketamine hydrochloride and 10 mg/kg of xylazine. Pupils were dilated with a topical application of 5% phenylephrine and 0.8% tropicamide. Six laser spots were induced in each eye using an Argon/dye laser (532 argon/dye laser, Coherent Medical Laser, Santa Clara, Calif.) by a single investigator as previously described (Zacks et al. (2002) Invest. Ophthalmol. Vis. Sci. 43(7): 2384-91; Poulaki et al. (2004) Am. J. Pathol. 165(2): 457-69).

Administration of 17-allylamino-17-demethoxygeldanamycin in vivo

To achieve steady drug levels in the circulation of animals, 17AAG (Calbiochem EMD Biosciences, San Diego, Calif.) or the vehicle (DMSO, Sigma, St. Louis, Mo.) was administered by slow intraperitoneal release from osmotic pumps (Alzet, Cupertino, Calif.) instead of repeated intraperitoneal injections. Immediately following the induction of choroidal neovascularization, osmotic pumps (Alzet, Cupertino, Calif.) were implanted as previously described (Poulaki et al. (2002) J. Clin. Invest. 109(6): 805-15). Two milligrams of 17AAG in 100 µl of DMSO (20 mg/ml) were inserted in each osmotic pump, which released 0.25 µl/hr for two weeks. The animals were separated into five categories: rats without any treatment, rats with laser treatment and DMSO-filled pumps, rats with laser treatment and 17AAG-filled pumps, rats with laser treatment and PDT treatment with DMSO-filled pumps, and rats with laser treatment and PDT treatment with 17AAG-filled pumps. The rats were sacrificed 1 and 7 days after the PDT treatment. The measurements of HIF-1a, NF-kB, p42/44 MAPK, VEGF and endostatin levels were performed 1 day after the PDT treatment.

Fluorescein Angiography

Fluorescein angiography ("FA") was performed 14 days after the initial laser treatment using a digital fundus camera system (model TRC 501A Topcon, Paramus, N.J.) and standard fluorescein filters to determine if CNV induction was successful. At 24 hours after verterporfin PDT, FA was performed to determine CNV closure. Each animal was given a bolus injection of 1 ml of 1% sodium fluorescein (Akorn Inc., Decatur, Ill.) in saline intraperitoneally, and the timer was started as soon as the fluorescein bolus was injected. All angiograms were evaluated in masked fashion by two independent retina specialists using grading standards regarding severity of CNV (baseline FAs) and CNV closure (24 hours FAs).

Photodynamic Therapy in Rats

PDT with verteporfin was performed on experimental CNV. Briefly, rats were anesthetized, and verteporfin at a dose of 3 mg/m$^2$ was injected into the tail vein of rats while they were immobilized in a stereotactic frame. The body surface area of each rat was determined based on their weight according to a nomogram developed by Gilpin (Gilpin et al. (1996) Burns 22(8): 607-1 1). One eye of each animal was selected, avoiding eyes that had large subretinal hemorrhage that the PDT spot could not cover. Fifteen minutes after the injection, laser light at 689 nm was administered through the pupil with a diode laser (Coherent Medical Laser, Santa Clara, Calif.) delivered through a slit lamp adaptor (Laserlink, Coherent Medical Laser, Santa Clara, Calif.). The diode laser spot size was set at 759 μm on the plane of the retina. The diode laser had a constant irradiance of 600 mW/cm$^2$, which was delivered for 17 or 42 seconds, to achieve a total energy dose of 10 J/cm$^2$.

Quantification of NF-kB and HIF-1a Activation

NF-kB and HIF-1a activation was analyzed using the Trans-AM NF-kB p65/NF-kB p50 Transcription Factor Assay Kit (Active Motif North America, Carlsbad, Calif.) according to the manufacturer's instructions. Briefly, two micrograms of a retinal nuclear extract were incubated with an oligonucleotide containing the consensus binding element for each of the transcription factors analyzed bound to a 96-well plate. After extensive washes, the transcription factor complexes bound to the oligonucleotide were incubated with an antibody directed against the NFkB p65 subunit or HIF-1a at a dilution 1:1000. After washes, the plates were subsequently incubated with a secondary antibody conjugated to horseradish peroxidase (1:1000), and the peroxidase reaction was quantified at 450 nm with a reference wavelength of 655 nm.

Preparation of Nuclear Extracts

Retinae from all the previously mentioned categories (3 each group) were isolated and homogenized as previously described (Poulaki et al. (2002) supra). Briefly, retinae were homogenized with a mechanical homogenizer in five pellet volumes of buffer A (20 mM Tris [pH 7.6], 10 mM KCl, 0.2 mM EDTA, 20% [by volume] glycerol, 1.5 mM MgCl$_2$, 2 mM DTT, 1 mM Na$_3$VO$_4$, and protease inhibitors; Roche Molecular Biochemicals Inc., Indianapolis, Ind.). The nuclei were pelleted (2,500 g, 10 minutes) and resuspended in two pellet volumes of buffer B (identical to buffer A except that KCl was increased to 0.42 M). Nuclear debris was removed by centrifugation (15,000 g, 20 minutes), and the supernatant was dialyzed against one exchange of buffer Z (20 mM Tris-HCl [pH 7.8], 0.1 M KCl, 0.2 mM EDTA, 20% glycerol) for at least 3 hours at 4° C. with Dialyze Z cassettes (Pierce Co., Rockford, Ill.). The protein concentration was measured using a Pierce Micro BCA™ Protein Assay Kit with serum albumin as a standard.

Enzyme-linked Immunoabsorbant Assay for VEGF and Endostatin

Each retina was homogenized in 100 μl of solution consisting of 20 mM imidazole hydrochloride, 100 mM KCl, 1 mM MgCl, 1 mM EGTA, 1% Triton, 10 mM NaF, 1 mM sodium molybdynate and 1 mM EDTA supplemented with a cocktail of protease inhibitors (Complete, Roche, Basel, Switzerland) prior to use. Samples were cleared by centrifugation for 10 min. at 13,000 rpm and assessed for protein concentration with the BCA assay (Micro BCA™ Protein Assay Kit, Pierce Co., Rockford, Ill.). The VEGF and endostatin protein levels were estimated with ELISA kits (R&D Systems, Minneapolis, Minn., and Calbiochem EMD Biosciences, San Diego, Calif., respectively) according to the manufacturer's instructions. The reaction was stopped, and the absorption was measured in an ELISA reader at 450 nm. All measurements were performed in duplicate. The tissue sample concentration was calculated from a standard curve and corrected for protein concentration.

Statistics

Differences in CNV induction between treatment groups were evaluated using chi-square tests. Lesions that did not show significant leakage were excluded from the statistical analysis.

Results 17-allylamino-17-demethoxygeldanamycin treatment potentiated the efficacy of verterporfin PDT for CNV closure through the HIF-1a and NF-kB mediated downregulation of angiogenic factors such as VEGF and upregulation of anti-angiogenic factors such as endostatin.

17-allylamino-17-demethoxvzeldanamycin Treatment Reduced Photodynamic Therapy-induced Angiographic Leakage in Laser-induced CNV To assess whether the 17AAG treatment influences angiographic leakage after PDT in a laser induced CNV model, the percentage of lesions that were closed in rats receiving PDT and 17AAG treatment was compared with the percentage of lesions that were closed in rats under the control condition (DMSO and PDT treatment). As an initial matter, at two weeks following CNV induction, 17AAG without PDT did not affect the angiographic leakage in a statistically significant manner as compared to control (DMSO without PDT). Specifically, in the vehicle (DMSO) treated animals (control), 32 out of 53 lesions showed the highest grade (IIB) of leakage, and in the 17AAG treated animals, 26 out of 47 lesions showed the highest grade (IIB) of leakage (P>0.05). Thus, 17AAG alone had no effect on leakage.

When lesions showing the highest grade of leakage were subjected to PDT treatment two weeks after induction of CNV and presentation of either 17AAG or DMSO, the combination of 17AAG and PDT showed a synergistic effect in closing leaky lesions. Specifically, the leakiest lesions (grade IIB) in rats that were induced by laser were treated with either 17AAG or DMSO (control) in combination with PDT, as described above. In the control group, 9 out of the 17 total lesions were closed one day after the PDT treatment and 6 out of the 17 total lesions were closed one week after PDT treatment. In the treatment group (17AAG), fourteen total lesions were treated and 12 out of the 14 total lesions were closed one day after the PDT treatment and 12 out of the 14 total lesions were closed one week after PDT treatment. Because 17AAG had no effect by itself (i.e., in the absence of PDT) and because a higher percentage of previously leaky lesions under the PDT and 17AAG condition were closed as compared with the percentage of closed lesions under the control (PDT and DMSO) condition, the effect of PDT in combination with 17AAG is synergistic rather than additive. Thus, the combination of PDT and 17AAG acts synergistically to treat a model of macular degeneration.

17-allylamino-17-demethoxyaeldanamycin treatment reduced photodynamic therapy-induced VEGF Upreeulation in Laser-induced CNV As previously described, retinal VEGF Levels Increased upon the Induction of CNV (4.25±0.018 μg VEGF/μg tissue in the laser-treated DMSO animals versus 2.15±0.3 μg VEGF/μg tissue in the controls, P<0.01). Photodynamic therapy increased the VEGF upregulation even further (5.58±0.8 μg VEGF/μg tissue in the PDT and laser treated animals versus 4.25±0.018 μg VEGF/μg tissue in the laser treated-DMSO animals (without PDT), P<0.01). 17-allylamino-17-demethoxygeldanamycin reduced the PDT-induced upregulation of VEGF levels (3.8±0.5 μg VEGF/μg tissue in the 17AAG and PDT treated animals versus 5.58±0.8 μg VEGF/μg tissue in the PDT and laser treated animals (without 17AAG), P<0.01). 17-allylamino-17-demethoxygeldanamycin administration in the laser treated (without PDT) animals did not reduce VEGF levels in a statistically significant manner (4.5±0.09 μg VEGF/μg tissue in the 17AAG laser treated animals versus 4.45±0.018 μg VEGF/μg tissue in the laser treated (without 17AAG) animals).

17-allylamino-17-demethoxygeldanamycin Treatment Reduced Photodynamic Therapy-induced HIF-1a and NF-kB Activation in Laser-induced CNV The retinal levels of HIF-1a activation did not increase in a statistically significant manner in the laser-treated animals (1.08±0.04 optical density units (O.D.)/μg tissue in the laser-treated animals versus 1.06±0.1 O.D./μg tissue in the non laser-treated animals P>0.05). Photodynamic therapy treatment upregulated the HIF-1a activation in a statistically significant manner (1.69±0.38 O.D./μg tissue in the PDT and laser treated animals versus 1.06±0.1 O.D./μg tissue in the laser treated animals (without PDT), P<0.01). 17-allylamino-17-demethoxygeldanamycin treatment decreased the PDT-induced upregulation of HIF-1a activation (0.946±0.06 O.D./μg tissue in the 17AAG and PDT treated animals versus 1.69±0.38 O.D./μg tissue in the PDT laser treated animals (without 17AAG)). 17-allylamino-17-demethoxygeldanamycin administration did not decrease HIF-1a activation in the laser-treated animals without PDT treatment (1.064±0.136 O.D./μg tissue in the 17AAG and laser treated animals versus 1.06±0.1 O.D./μg tissue in the laser treated animals (without 17AAG) P>0.05).

The retinal levels of NF-kB activation increased in a statistically significant manner in the laser-treated animals (10.12±0.74 O.D./μg tissue in the laser-treated animals versus 5±0.86 O.D./μg tissue in the non laser-treated animals, P<0.01). Photodynamic therapy treatment upregulated the NF-kB activation in a statistically significant manner (13.7±0.3 O.D./μg tissue in the PDT and laser treated animals versus 10.12±0.74 O.D./μg tissue in the laser treated animals (without PDT), P<0.01). 17-allylamino-17-demethoxygeldanamycin treatment decreased the PDT-induced upregulation of NF-kB activation (5.9±0.045 O.D./μg tissue in the 17AAG and PDT treated animals versus 13.7±0.3 O.D./μg tissue in the PDT laser treated animals (without 17AAG)). 17-allylamino-17-demethoxygeldanamycin administration did not decrease NF-kB activation in the laser-treated animals without PDT treatment (9.54±1.47 O.D./μg tissue in the 17AAG and laser treated animals versus 10.12±0.74 O.D./μg tissue in the laser treated animals (without 17AAG), P>0.05).

17-allylamino-17-demethoxyaeldanamycin Treatment Reduced Photodynamic Therapy-induced p42/44 MAPK Activation in Laser-induced CNV The retinal levels of p42/44 MAPK activation increased but not in a statistically significant manner in the laser-treated animals (603±1 O.D./μg tissue in the laser-treated animals versus 491±75 O.D./μg tissue in the non laser-treated animals P>0.05). Photodynamic therapy treatment upregulated p42/44 MAPK activation in a statistically significant manner (923.7±45 O.D./μg tissue in the PDT and laser treated animals versus 603±1 O.D./μg tissue in the laser treated animals (without PDT), P<0.01). 17-allylamino-17-demethoxygeldanamycin treatment decreased the PDT-induced upregulation of p42/44 activation (417±6 O.D./μg tissue in the 17AAG and PDT treated animals versus 923±45 O.D./μg tissue in the PDT laser treated animals (without 17AAG)). 17-allylamino-17-demethoxygeldanamycin administration did not decrease p42/44 MAPK activation in the laser-treated animals without PDT treatment (560±22 O.D./μg tissue in the 17AAG and laser treated animals versus 603±1 O.D./μg tissue in the laser treated animals (without 17AAG), P>0.05).

17-allylamino-17-demethoxyaeldanamycin Treatment Induces Upregulation of Endostatin in Laser-induced CNV Animals Treated with Photodynamic Therapy The retinal levels of endostatin decreased in a statistically significant manner in the laser-treated animals (15.7±2.8 O.D./μg tissue in the laser-treated animals versus 406±180 O.D./μg tissue in the non laser-treated animals P<0.01). Photodynamic therapy treatment upregulated endostatin expression but not in a statistically significant manner (122.5±75.3 O.D./μg tissue in the PDT and laser treated animals versus 15.7±2.8 O.D./μg tissue in the laser treated animals without PDT, P>0.05). 17-allylamino-17-demethoxygeldanamycin treatment increased endostatin upregulation beyond the levels produced by PDT-induced upregulation alone, in a statistically significant manner (258±6 O.D./μg tissue in the 17AAG and PDT treated animals versus 15.7±2.8 O.D./μg tissue in the laser treated animals). 17-allylamino-17-demethoxygeldanamycin administration did not increase endostatin in the laser-treated animals without PDT treatment (32.34±6.11 O.D./μg tissue in the 17AAG and laser treated animals versus 15.7±2.8 O.D./μg tissue in the laser treated animals P>0.05).

Treatment with PDT and 17AAG produced a synergistic effect on endostatin levels. Because neither 17AAG alone or PDT alone had a significant effect in retinal endostatin levels and because only the combination of PDT and endostatin succeeded in increasing the retinal endostatin levels to a statistically significant degree, the effect of PDT in combination with 17AAG is synergistic rather than additive. Thus, the combination of PDT and 17AAG acts synergistically to increase endostatin levels in a model of macular degeneration.

Discussion

The experiments described above investigated the efficacy of 17AAG in combination with PDT in a rat model of laser-induced neovascularization. Without being bound by theory, these experiments indicate that 17AAG in combination with PDT decreases CNV-associated angiographic leakage by decreasing the activation of transcription factors such as HIF-1a and NF-kB and signaling kinases such as p42/44 MAPK. These experiments also showed that 17AAG increased the expression of anti-angiogenic molecules such as endostatin and decreased angiogenic growth factors such as VEGF in animals receiving PDT.

PDT treatment induces the upregulation of VEGF. The PDT-induced upregulation of growth factors such as VEGF has been identified as a potential cause of the persistent angiographic leakage that characterizes a PDT failure and that necessitates further re-treatments (Ferrario et al. (2000) Cancer Res. 60: 4066-69). It has been hypothesized that the reduction in vascular perfusion that is caused by the microvascular injury mediated by PDT is responsible for the hypoxia of the treated tissue that drives the expression of VEGF (van Geel et al. (1996) Br. J. Cancer 73: 288-293). The PDT-induced VEGF upregulation was originally observed in treated tumors, and it was used as a positive control for tissue hypoxia (Levy et al. (1995) J. Biol. Chem. 270: 13333-40). It has been hypothesized that tumor-associated macrophages are the source of the various growth factors that are activated by the treatment and recruited to the treated area. Possibly, blood-derived leukocytes are recruited to the PDT-treated retina and secrete VEGF.

The signal transduction pathway that mediates the PDT-induced upregulation of VEGF includes the activation of HIF-1a, NF-kB and P42/44 MAPK. In the rat model of STZ-induced diabetes, it has been shown that VEGF upregulation by IGF-I and insulin is mediated through HIF-1a and NF-kB responsive elements in the VEGF promoter (Poulaki et al. (2002) J. Clin. Invest. 109(6): 805-15). This example shows that PDT induces the upregulation of HIF-1a and NF-kB and the activation of P42/44 MAPK. The hypoxic environment that is generated by the photosensitizer-induced microvascular injury is responsible for the post-transcriptional stabilization of the HIF-1a protein (Levy et al. (1995) supra). Hypoxia and hypoxia-mimicking agents like cobalt chloride induce HIF-1a by disrupting its association with the von-Hippel Lindau protein and by impairing its degradation by the proteasome (Levy et al. (1995) supra). It has been suggested that the hypoxia-induced stabilization of HIF-1a is mediated through an oxygen sensor molecule that transduces a low oxygen concentration. However, the generation of free radical species primarily from the photosensitizer, that is a free radical itself, and from the subsequent hypoxia, induces NF-kB directly as it was previously shown in other systems (Zheng et al. (2004) 26(8): 884-892). Although HIF-1a was activated only upon the PDT treatment in laser-induced CNV, possibly due to the hypoxic environment caused by the vascular occlusion, NF-kB was activated in laser-induced CNV, highlighting the role of this transcription factor in the pathogenesis of the choroidal neovascular membrane. Without being bound to theory, it may be that VEGF upregulation in CNV is more dependent on factors like NF-kB, whereas, upon PDT treatment, factors such as HIF-1a start to play a more active role. NF-kB and HIF-1a activity has been found to be dependent upon the activation of PI-3K and MAPKs such as p38 and p42/44 in several other systems (Garcia-Garcia et al. (2001) J. Leukoc. Biol. 70(4): 649-58 (#179)). Although upregulation of p38 MAPK has not been detected in a statistically significant manner, it seems that p42/44 MAPK was significantly upregulated in laser-induced CNV upon PDT treatment, probably mediating the HIF-1a-induced and NF-kB-induced VEGF upregulation. It was previously shown that p38 MAPK is transiently activated upon PDT treatment, whereas p42/44 MAPK activation is more sustained and can be detected even after 12 hours of treatment. That may account for the seemingly differential activation that was detected 24 hours after the PDT treatment in the laser-induced CNV model.

This example shows that treatment with 17AAG, and more generally ansamycin analogs and/or Hsp90 inhibitors, downregulate PDT-induced upregulation of HIF-1a, NF-kB, p42/44 MAPK, and VEGF. It has been previously demonstrated that 17AAG has an inhibitory effect on the activation of the above-mentioned signal transduction molecules (Poulaki et al. (2004) Am. J. Pathol. 165(2): 457-69). Geldanamycin was found to exert multiple inhibitory effects on the NF-kB activation directly by blocking the nuclear translocation of NF-kB in respiratory epithelium in vitro after it is released from IkBa (Malhotra et al. (2001) Am. J. Respir. Cell Mol. Biol. 25(1): 92-97) or indirectly through Hsp90 and the induction of a heat shock response (Conde et al. (1997) J. Mol. Cell Cardiol. 29(7): 1927-38). It also has been demonstrated previously that 17AAG inhibits the activation of p42/44 and Akt, which may also account for the observed downregulation of the HIF-1a activation. The inhibition of HIF-1a and NF-kB may directly account for the observed downregulation of the PDT-induced VEGF upregulation at the transcriptional level through the multiple relevant responsive elements that the VEGF promoter has (Wax et al. (2003) Arthritis Rheum. 48(2): 541-50). Alternatively, 17AAG may destabilize the inflammatory cytokine transcripts through the inhibition of the p38 MAPK-dependent recruitment of trans-acting factors to adenine/uridine rich elements in their 3' untranslated regions that prevent their degradation (Wax et al. (2003) supra).

The 17AAG-induced reduction of the VEGF expression levels may account for the increased efficacy of the combined 17AAG and verteporfin PDT in inducing CNV closure. VEGF is known to play a central role in the pathogenesis of choroidal neovascularization and also in the recurrence of vascular leakage after PDT. According to these experiments, the effect of 17AAG in combination with PDT was even more enhanced 7 days after the treatment, showing that the 17AAG-induced downregulation of PDT-induced VEGF upregulation can have a beneficial effect to the long term success of PDT in CNV closure. Surprisingly, 17AAG induced an upregulation of endostatin levels, a natural inhibitor of angiogenesis. Photodynamic therapy itself induces a moderate upregulation of the endogenous endostatin levels, although not in a statistically significant manner, whereas 17AAG enhances this upregulation to a level of statistical significance. Without being bound to theory, it may be that the upregulation of endostatin levels by PDT alone is not sufficient to ensure long-term inhibition of the angiographic leakage from the neovascular complexes, whereas the combination of 17AAG and PDT ensures adequate levels and has a more potent anti-angiogenic effect.

17AAG increased the efficacy of verteporfin PDT in CNV closure by inhibiting the PDT-induced upregulation of p42/44 MAPK, HIF-1a and NF-kB activation and subsequent VEGF expression. 17-allylamino-17-demethoxygeldanamycin treatment also collaborated with verteporfin-PDT in the upregulation of antiangiogenic growth factors such as endostatin. 17-allylamino-17-demethoxygeldanamycin and other members of the classes of drugs that it belongs to, such as geldanamycin and other ansamycin analogs and/or Hsp90 inhibitors, are therefore useful in improving the efficacy (in some cases synergistically) of verteporfin PDT in age-related macular degeneration as well as other disorders involving unwanted CNV.

To the extent necessary, any ansamycin analog, Hsp90 inhibitor, candidate ansamycin analog, and/or candidate Hsp90 inhibitor can be tested for activity using, for example, the methods described in this example. For example, the methods used to measure 17AAG's influence on angiographic leakage or VEGF upregulation can be used to determine if the compound enhances lesion closure or decreases PDT-induced VEGF upregulation. To the extent a compound has one or more of these activities, it can be considered useful according to the invention.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Incorporation by Reference

The entire disclosure of each of the patent documents and scientific publications disclosed hereinabove is expressly incorporated herein by reference for all purposes.

What is claimed is:

1. A method of treating unwanted choroidal neovasculature (CNV) in a mammal, the method comprising the steps of:
   (a) performing photodynamic therapy on the unwanted choroidal neovasculature; and
   (b) administering to the mammal a synergistically effective amount of 17-allylamino-17-demethoxygeldanamycin (17AAG), wherein the combination of steps (a) and (b) results in a synergistic level of CNV closure in the mammal.

2. The method of claim 1, wherein step (b) occurs before step (a).

3. The method of claim 1, wherein step (b) occurs simultaneously with step (a).

4. The method of claim 1, wherein step (b) occurs after step (a).

5. The method of claim 1, wherein the mammal is a primate.

6. The method of claim 5, wherein the primate is a human.

7. The method of claim 1, wherein step (a) comprises (i) administering a photosensitizer to the mammal, and (ii) irradiating the photosensitizer when disposed within the choroidal neovasculature.

8. The method of claim 7, wherein the photosensitizer is an amino acid derivative, an azo dye, a xanthene derivative, a chlorin, a tetrapyrrole derivative, or a phthalocyanine.

9. The method of claim 8, wherein the photosensitizer is lutetium texaphyrin, a benzoporphyrin, a benzoporphyrin derivative, a hematoporphyrin, or a hematoporphyrin derivative.

10. An improved photodynamic therapy-based method of treating unwanted choroidal neovasculature (CNV) in a mammal, the improvement comprising:
    administering to the mammal a synergistically effective amount of 17-allylamino-17-demethoxygeldanamycin (17AAG) so that the 17AAG in combination with photodynamic therapy induces a synergistic level of CNV closure in the mammal.

11. The method of claim 10, wherein the 17AAG decreases photodynamic therapy-induced upregulation of vascular endothelial growth factor.

12. The method of claim 10, wherein the photodynamic therapy uses a benzoporphyrin derivative photosensitizer.

13. The method of claim 10, further comprising administering an effective amount of an anti-VEGF aptamer.

14. The method of claim 10, further comprising administering an effective amount of an anti-VEGF antibody.

15. The method of claim 10, further comprising administering an effective amount of an anti-VEGF siRNA.

16. The method of claim 10, wherein the method ameliorates the symptoms of age-related macular degeneration.

* * * * *